(12) United States Patent
Goto et al.

(10) Patent No.: US 8,208,143 B2
(45) Date of Patent: Jun. 26, 2012

(54) EXHAUST GAS ANALYZER (75) Inventors: Katsutoshi Goto, Okazaki (JP); Masahiro Yamakage, Anjo (JP); Yoshihiro Deguchi, Yokohama (JP); Taketoshi Yamaura, Nagasaki (JP)

(73) Assignees: Toyota Jidosha Kabushiki Kaisha, Toyota-shi, Aichi-ken (JP); Mitsubishi Heavy Industries, Ltd., Tokyo (JP)

( * ) Notice: Subject to any disclaimer, the term of this patent is extended or adjusted under 35 U.S.C. 154(b) by 450 days.

(21) Appl. No.: 11/918,650

(22) PCT Filed: Apr. 28, 2006

(86) PCT No.: PCT/JP2006/309360
§ 371 (c)(1),
(2), (4) Date: Oct. 17, 2007

(87) PCT Pub. No.: WO2006/118347
PCT Pub. Date: Nov. 9, 2006

(65) Prior Publication Data
US 2009/0039284 A1 Feb. 12, 2009

(30) Foreign Application Priority Data

Apr. 28, 2005 (JP) ................................. 2005-132822

(51) Int. Cl.
*G01N 21/00* (2006.01)
(52) U.S. Cl. ........................................ 356/432; 356/438
(58) Field of Classification Search .................. None
See application file for complete search history.

(56) References Cited

U.S. PATENT DOCUMENTS 2,656,594 A * 10/1953 Westling .......................... 29/428

(Continued)

FOREIGN PATENT DOCUMENTS

DE 103 09 604 A1 9/2004

(Continued)

OTHER PUBLICATIONS

Supplementary European Search Report for EP Application No. 06 73 2512.6, mailed Mar. 17, 2010.

(Continued)

*Primary Examiner* — Tarifur Chowdhury
*Assistant Examiner* — Gordon Stock, Jr.
(74) *Attorney, Agent, or Firm* — Finnegan, Henderson, Farabow, Garrett & Dunner, LLP (57) ABSTRACT

An exhaust gas analyzer capable of real-time analysis of the concentration, temperature, and the like of an exhaust gas component in a cross-section of an exhaust path in a spot-wise manner reduces analysis cost. An exhaust gas analyzer (10) comprises sensor units (11) to (14) disposed along the exhaust path, which comprises an exhaust manifold (3) for the engine (2) discharging exhaust gas, an exhaust tube (4), a first catalyst device (5), a second catalyst device (6), a muffler (7), and an exhaust pipe (8). Each sensor unit includes an optical fiber (25) for irradiating the exhaust gas with laser light, and a detector (26) for receiving the laser light emitted by the optical fiber that has been transmitted through the exhaust gas. Based on the laser light received by the detector, the condition of an exhaust gas component, such as its concentration, temperature, and the like, is measured for the analysis of the exhaust gas. The sensor unit has a through-hole (21) allowing the passage of exhaust gas that is formed in a shape matched with a cross-sectional shape of the exhaust path. The infrared laser light R is emitted via the optical fiber (25) into the through-hole (21), travels across the exhaust path, and is then received by the detector (26).

13 Claims, 6 Drawing Sheets

U.S. PATENT DOCUMENTS

| | | | | |
|---|---|---|---|---|
| 2,663,586 | A * | 12/1953 | Gardes | 292/256.75 |
| 3,207,026 | A * | 9/1965 | Lovie et al. | 356/435 |
| 4,225,243 | A * | 9/1980 | Typpo | 356/409 |
| 4,364,226 | A * | 12/1982 | Croset et al. | 60/276 |
| 4,381,153 | A * | 4/1983 | Bohl et al. | 356/437 |
| 4,432,649 | A * | 2/1984 | Krause | 356/438 |
| 5,049,742 | A * | 9/1991 | Hosonuma et al. | 250/301 |
| 5,096,834 | A * | 3/1992 | Saito | 436/139 |
| 5,173,749 | A * | 12/1992 | Tell et al. | 356/437 |
| 5,185,645 | A | 2/1993 | Sartorius et al. | |
| 5,202,570 | A | 4/1993 | Tanaka et al. | |
| 5,261,415 | A * | 11/1993 | Dussault | 600/532 |
| 5,275,553 | A * | 1/1994 | Frish et al. | 431/76 |
| 5,327,356 | A * | 7/1994 | Lang et al. | 702/22 |
| 5,381,010 | A | 1/1995 | Gordon | |
| 5,585,636 | A | 12/1996 | Dollansky | |
| 5,773,841 | A * | 6/1998 | Aqui | 250/573 |
| 5,811,812 | A * | 9/1998 | Williams et al. | 250/343 |
| 5,818,578 | A | 10/1998 | Inman et al. | |
| 5,835,230 | A * | 11/1998 | McAndrew et al. | 356/437 |
| 6,154,284 | A | 11/2000 | McAndrew et al. | |
| 6,271,522 | B1 * | 8/2001 | Lindermeir et al. | 250/341.1 |
| 6,560,545 | B2 * | 5/2003 | Stedman et al. | 702/28 |
| 6,710,878 | B1 * | 3/2004 | Dean et al. | 356/436 |
| 6,809,825 | B2 * | 10/2004 | Kaufmann | 356/439 |
| 8,085,404 | B2 | 12/2011 | Yamakage et al. | |
| 2003/0160174 | A1 * | 8/2003 | Grant et al. | 250/339.13 |
| 2004/0237505 | A1 | 12/2004 | Leipertz | |
| 2009/0039284 | A1 | 2/2009 | Goto et al. | |
| 2009/0095918 | A1 * | 4/2009 | Iwase et al. | 250/432 R |
| 2009/0164138 | A1 * | 6/2009 | Goto et al. | 702/24 |
| 2009/0229250 | A1 * | 9/2009 | Yamakage et al. | 60/276 |
| 2009/0323068 | A1 * | 12/2009 | Yamakage et al. | 356/437 |

FOREIGN PATENT DOCUMENTS

| | | | |
|---|---|---|---|
| EP | 0 768 521 | | 4/1997 |
| EP | 1 398 617 | A1 | 3/2004 |
| JP | 58-090147 | A | 5/1983 |
| JP | 62-016371 | B | 4/1987 |
| JP | 63-107845 | | 7/1988 |
| JP | 01-235834 | A | 9/1989 |
| JP | 03-277945 | A | 12/1991 |
| JP | 05-026804 | A | 2/1993 |
| JP | 5-77023 | | 10/1993 |
| JP | 8-043305 | | 2/1996 |
| JP | 9-222392 | | 8/1997 |
| JP | 2837442 | | 10/1998 |
| JP | 11-083734 | | 3/1999 |
| JP | 11-325427 | | 11/1999 |
| JP | 2000-074830 | | 3/2000 |
| JP | 2000074830 | A * | 3/2000 |
| JP | 2001-074653 | | 3/2001 |
| JP | 2001-124674 | | 5/2001 |
| JP | 2001-174410 | | 6/2001 |
| JP | 2002-131198 | | 5/2002 |
| JP | 2003-344244 | | 12/2003 |
| JP | 2004-055183 | | 2/2004 |
| JP | 2004-117259 | | 4/2004 |
| JP | 2006-184180 | | 7/2006 |

OTHER PUBLICATIONS

Extended Search Report for EP Application No. 07806294 dated Aug. 22, 2011.

Office Action from the U.S. Patent and Trademark Office for U.S. Appl. No. 12/309,584 dated Feb. 4, 2011.

* cited by examiner

FIG. 6 A
SIGNAL INTENSITY

FIG. 6 B
SIGNAL INTENSITY

EXHAUST GAS ANALYZER

TECHNICAL FIELD

The invention relates to an exhaust gas analyzer for analyzing components contained in exhaust gas emitted by an internal combustion engine of an automobile, for example. Particularly, the invention relates to an exhaust gas analyzer capable of simultaneously measuring the concentrations of multiple components in the exhaust gas in a cross-section of the passageway of the gas.

BACKGROUND ART

As a conventional example of the exhaust gas analyzer of the aforementioned type, Patent Document 1 discloses a vehicle-mounted HC measuring apparatus. This vehicle-mounted HC measuring apparatus enables the mounting in the vehicle of: an NDIR (non-dispersive infrared) gas analyzer for continuously measuring HC (hydrocarbon) concentrations in the exhaust gas flowing in the exhaust tube connected to the engine; an exhaust gas flowmeter for continuously measuring the flow rate of exhaust gas flowing in the exhaust tube; and an operational processing circuit for continuously calculating the amount of THC (total hydrocarbon) in the exhaust gas by calculating the outputs of the NDIR gas analyzer and the exhaust gas flowmeter.

There are a variety of other exhaust gas measuring apparatuses and analyzers that employ the NDIR (non-dispersive infrared) method, the FID (flame ionization detector) method, or the CLD (chemical luminescence detector) method. These measuring methods in all their measurement principles require the use of reference gas.

Patent Document 1: JP Patent Publication (Kokai) No. 2004-117259A

The exhaust gas analyzer disclosed in Patent Document 1 measures the concentration of the THC component, for example, in the exhaust gas by sampling the exhaust gas in the exhaust path as it is emitted by the internal combustion engine of the vehicle running on the actual road, using infrared absorption or some other analysis technique.

However, in such exhaust gas analyzer, the flow of the exhaust gas in the exhaust path is stirred as the exhaust gas is sampled, thereby preventing a real-time analysis of the condition of exhaust gas as it flows in the exhaust path. As a result, it is impossible to measure the concentration of each component in the exhaust gas as it flows in the exhaust path after being emitted by the internal combustion engine.

It is therefore an object of the invention to provide an exhaust gas analyzer which enables the concentrations of components of the exhaust gas emitted by the internal combustion engine of an automobile or the like to be measured accurately as it flows in the exhaust path.

DISCLOSURE OF THE INVENTION

In order to achieve the aforementioned object, the invention provides an exhaust gas analyzer which comprises a sensor unit disposed in an exhaust path via which exhaust gas is discharged from an internal combustion engine, the sensor unit comprising an irradiation unit for irradiating the exhaust gas with laser light, and a photoreceiving unit for receiving the laser light emitted by the irradiation unit that has been transmitted through the exhaust gas. The concentration, temperature, and the like of an exhaust gas component are measured on the basis of the laser light received by the photoreceiving unit for analyzing the exhaust gas. The sensor unit includes a through-hole allowing the passage of the exhaust gas that is formed in a shape matched with a cross-sectional shape of the exhaust path. The laser light is shone by the irradiation unit into the through-hole and is received by the photoreceiving unit across the exhaust path. The exhaust path refers to the passage via which the exhaust gas emitted by the engine flows; it may extend from the exhaust holes in the engine main body to a muffler at the end, or to an exhaust pipe that protrudes from the muffler, depending on the particular embodiment. The exhaust gas analyzer of the invention is used for measuring the concentration or temperature of an exhaust gas component in the exhaust gas that flows in or emitted via the exhaust path.

Thus, in accordance with the exhaust gas analyzer of the invention, the laser light for measuring the concentration, temperature, and the like of an exhaust gas component is shone into the through-hole in which the exhaust gas passes, transmitted across the exhaust gas, and received by the photoreceiving unit. Thus, the apparatus enables the measurement of the concentration, temperature and the like of an exhaust gas component in a cross-section of the exhaust path. Further, the through-hole through which the exhaust gas passes is matched in shape with the cross-sectional shape of the exhaust path, so that no disturbance is caused in the flow of exhaust gas and no exhaust loss is caused, thereby enabling an accurate measurement. Preferably, the laser light travels across the exhaust path perpendicularly; however, it may intersect the exhaust path at an angle. By thus emitting the laser light into exhaust gas and measuring its attenuation as it passes through the exhaust gas, absorption of a particular wavelength can be detected and the concentration of an exhaust gas component can be calculated.

The sensor unit can be easily installed in the exhaust path of an automobile, for example. The laser light is emitted into the exhaust gas within the through-hole, transmitted through and attenuated by the exhaust gas, and then received. Based on the received laser light, the concentration or temperature of an exhaust gas component is measured. In this way, real-time measurement is possible, so that the high-temperature exhaust gas immediately after being discharged from the internal combustion engine can be measured. Furthermore, no reference gas or the like is required for measurement, so that cost can be reduced and measurement can be made easily and instantaneously.

The sensor unit is installed with the plate-shaped sensor main body sandwiched between members of which the exhaust path is composed. The exhaust path has a circular cross-sectional shape; preferably, the sensor main body has a through-hole formed therein which has a basic circular shape with the same diameter as the circular cross-section of the exhaust path. In this way, the sensor unit, with the through-hole having the basic circular shape with the same diameter, is installed in the exhaust path having a circular cross-sectional shape. As a result, the disturbance in the flow of exhaust gas caused by the sensor unit can be reduced, and no exhaust loss is caused, thereby preventing the performance of the internal combustion engine from being affected, and enabling efficient discharge of gas and accurate measurement. Further, the installment of the sensor unit in the exhaust path is facilitated.

Preferably, the through-hole has a reflecting portion formed on the inside of its internal peripheral surface, wherein the laser light emitted by the irradiation unit is reflected by the reflecting portion before it is received by the photoreceiving unit. In this configuration of the exhaust gas analyzer, the laser light shone into the through-hole is reflected by the reflecting portion formed on the internal peripheral surface of the through-hole, so that the laser light travels a long distance in the exhaust gas. As a result, the attenuation of the laser light as it is transmitted through the exhaust gas increases, which allows for the accurate measurement of the concentration or temperature of an exhaust gas component.

Preferably, the reflecting portion comprises two reflecting plates disposed opposite each other and in parallel such that they face the inside of the through-hole, so that the laser light is reflected perpendicular to the exhaust path. In this configuration of the exhaust gas analyzer, the laser light is reflected between the two parallel reflecting plates across the through-hole, thereby extending the transmission distance within the exhaust gas. As a result, the optical path of the laser light can be extended and higher utilization efficiency can be achieved. Because the ratio of the optical intensity of the emitted laser light to the optical intensity of the transmitted laser light can be reduced, the concentration and temperature of an exhaust gas component in a cross-section of the exhaust path can be measured accurately.

Preferably, the laser light emitted by irradiation unit comprises a multiplexing of laser light having absorption wavelengths matched with a plurality of components of the exhaust gas. When the laser light emitted by the irradiation unit of the exhaust gas comprises a multiplexing of a plurality of wavelengths, the concentration of a plurality of components in the exhaust gas or the exhaust gas temperature can be accurately measured simultaneously in accordance with the wavelengths of the laser light for the analysis of the exhaust gas.

Preferably, such sensor units are installed at a plurality of locations along the exhaust path. When the sensor units are installed at a plurality of locations along the exhaust path, the condition of the exhaust gas along the exhaust path can be easily monitored. Because the sensor unit of the exhaust gas analyzer of the invention measures the concentration of an exhaust gas component by laser light irradiation, high-temperature measurement is possible. Thus, the sensor unit can be installed in the exhaust path immediately following the exhaust valves, thereby allowing for high-temperature measurement of the concentration of a component.

BRIEF DESCRIPTION OF THE DRAWINGS

FIG. 5a is a chart for the description of signal intensity at low temperature; FIG. 5b is a chart for the description of signal intensity at high temperature.

BEST MODE OF CARRYING OUT THE INVENTION

Figure 1:
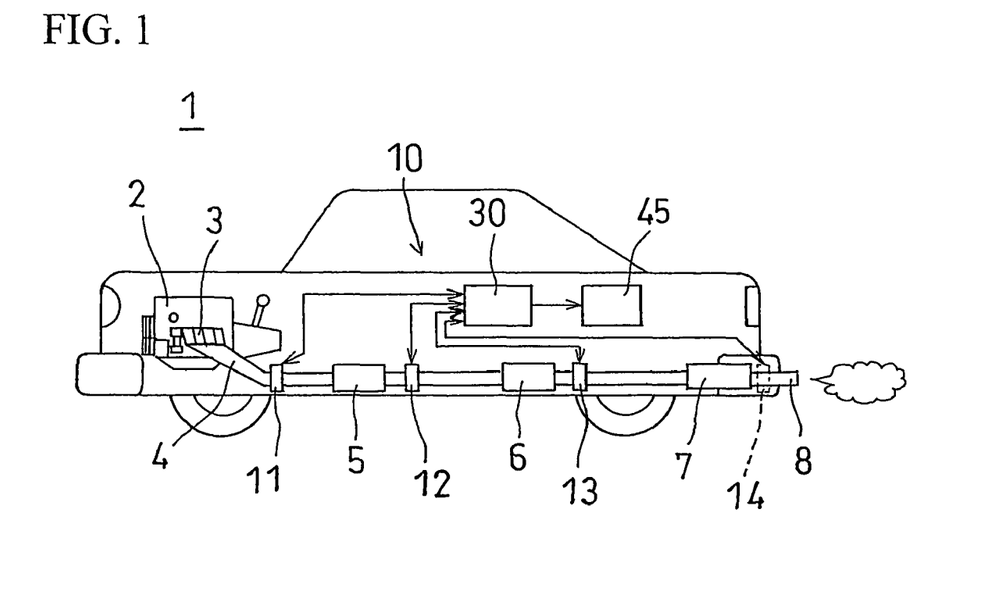
FIG. 1 shows a diagram of main portions of the exhaust gas analyzer mounted on a vehicle according to an embodiment of the invention.
Figure 2:
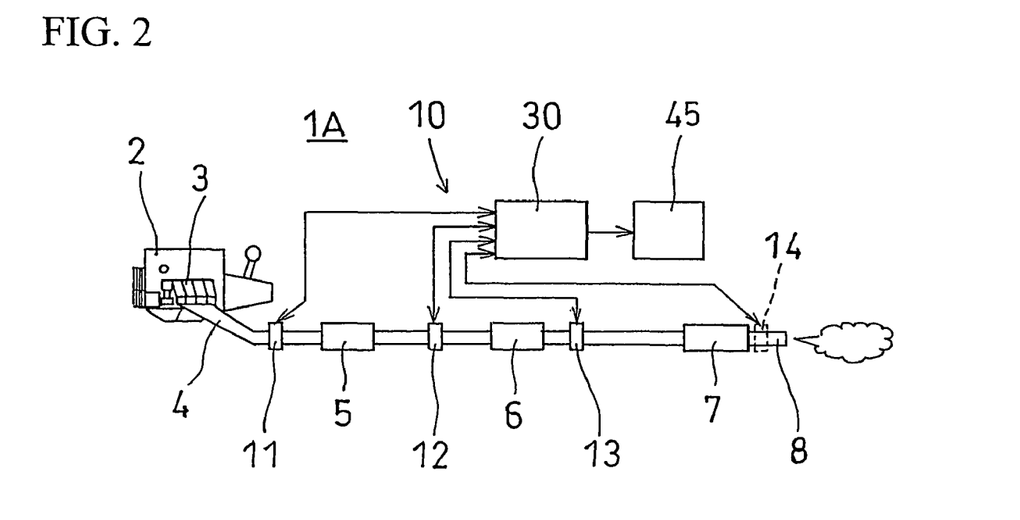
FIG. 2 shows a diagram of main portions of the exhaust gas analyzer mounted on an engine bench according to another embodiment of the invention.
Figure 3:
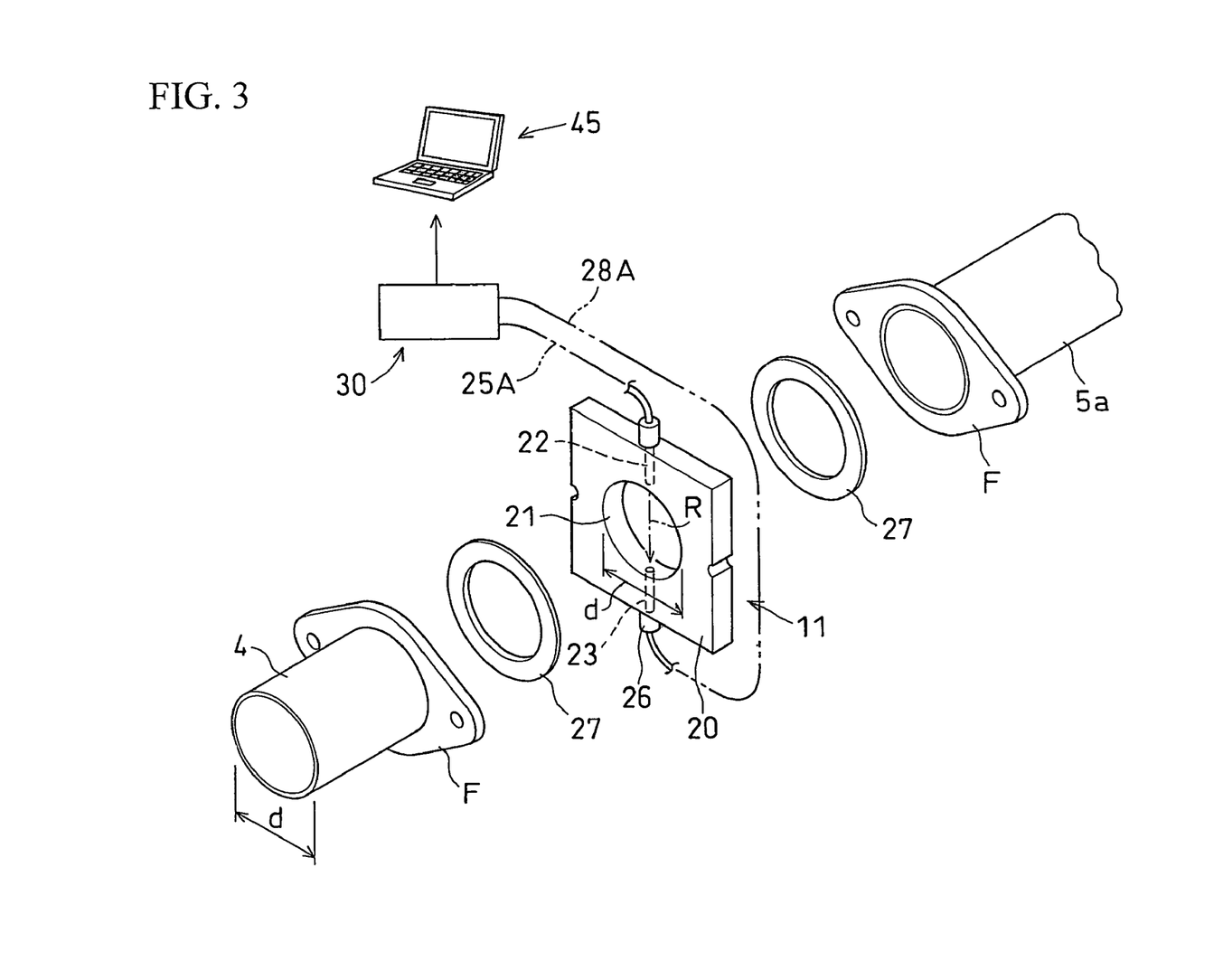
FIG. 3 shows a diagram of main portions of the exhaust gas analyzer, including an exploded perspective view of a single sensor unit.
Figure 4:
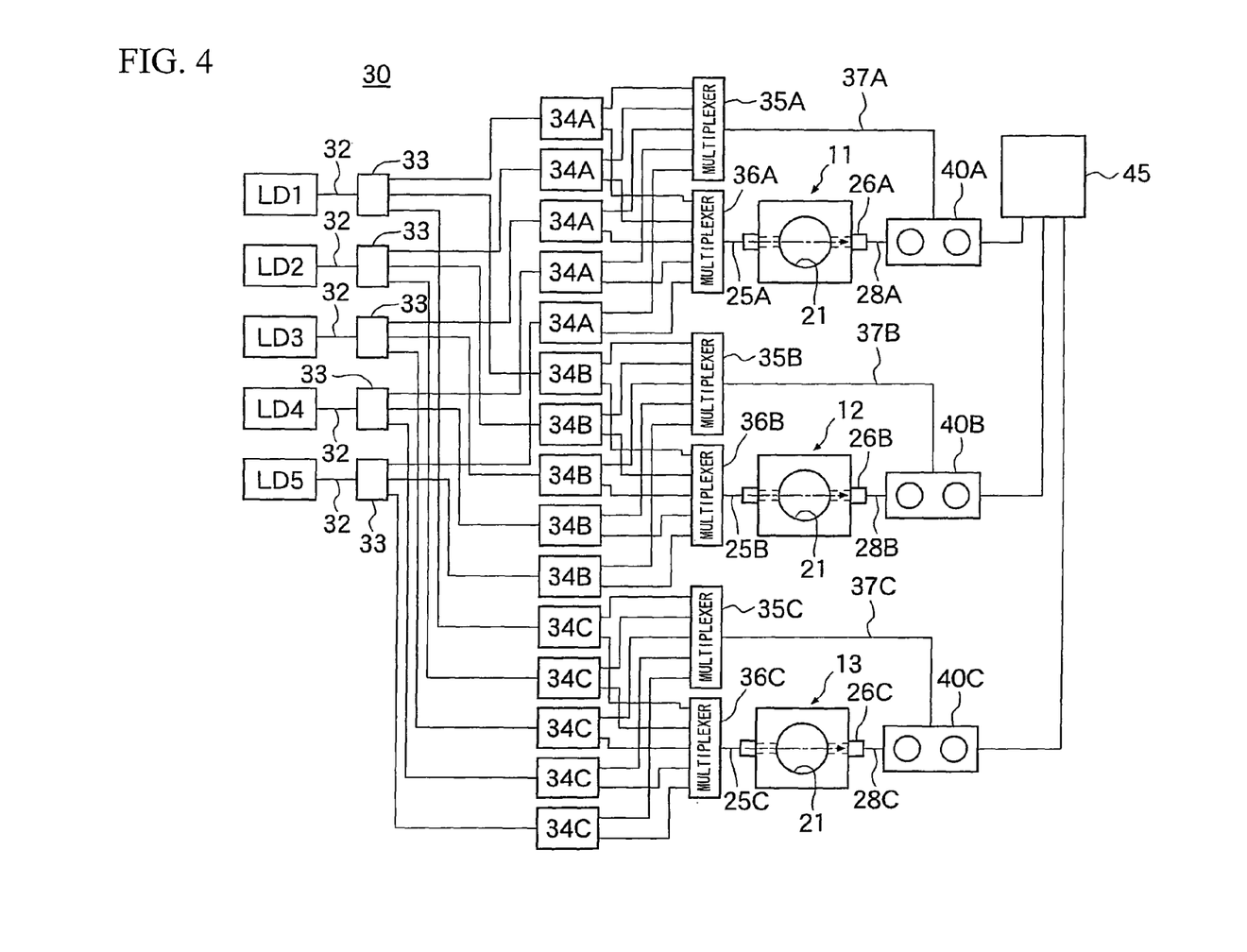
FIG. 4 shows a block diagram of an overall configuration of the exhaust gas analyzer, including a laser oscillation/photoreception controller and a signal analyzer.

In the following, an exhaust gas analyzer according to an embodiment of the invention will be described with reference to the drawings. FIG. 1 shows a diagram of an automobile in which the exhaust gas analyzer of the present embodiment is mounted. FIG. 2 shows a diagram of the exhaust gas analyzer of FIG. 1 installed on an engine bench. FIG. 3 shows a diagram of the exhaust gas analyzer including an exploded perspective view of main portions of a sensor unit. FIG. 4 shows a block diagram of an overall configuration of the exhaust gas analyzer, including a laser oscillation/photoreception controller and a signal analyzer.

Throughout FIGS. 1 to 4, the exhaust gas analyzer of the present embodiment is used for analyzing the exhaust gas emitted by an engine 2 installed on an automobile 1. It is also used, as shown in FIG. 2, for analyzing the exhaust gas from the engine 2 installed on an engine bench 1A. The exhaust gas emitted through each cylinder of the engine 2 join together in an exhaust manifold 3. The gas passes through an exhaust tube 4 and is then introduced into a first catalyst device 5, followed by a second catalyst device 6. Thereafter, the gas is emitted to the atmosphere out of an exhaust pipe 8 via a muffler 7. The exhaust path thus consists of the exhaust manifold 3, the exhaust tube 4, the first catalyst device 5, the second catalyst device 6, the muffler 7, and the exhaust pipe 8. The exhaust gas emitted by the engine 2 is purified by the two catalyst devices 5 and 6, and its noise and pressure are reduced by the muffler 7, before it is emitted to the atmosphere. The muffler may be composed of a main muffler and a sub-muffler.

The members of which the exhaust path is composed are connected via their flanges that are bolted, for example. For example, the first and second catalyst devices 5 and 6 each have exhaust pipe portions connected to the upstream and downstream sides of their main bodies having larger diameters, and flanges F, F are fixedly attached to the ends of the exhaust pipe portions by welding, for example. The muffler 7 has exhaust pipe portions connected to the upstream and downstream sides of its main body having a larger diameter, and flanges F, F are fixedly attached to the ends of the exhaust pipe portions. The exhaust pipe 8 at the end is directly fixed to the muffler 7 by welding, for example. Thus, the members of which the exhaust path is composed are connected via their flanges, and the exhaust path, through which exhaust gas passes, is formed such that it has a circular cross-sectional shape with a diameter of d.

The exhaust gas analyzer 10 of the present embodiment includes a plurality of sensor units 11 to 14 disposed at a plurality of locations along the exhaust path. A first sensor unit 11 is disposed between the first catalyst device 5 and the engine. A second sensor unit 12 is disposed downstream of the first catalyst device 5. A third sensor unit 13 is disposed downstream of the second catalyst device 6. A fourth sensor unit 14 is installed on the exhaust pipe 8 downstream of the muffler 7. The sensor unit 14 may be disposed somewhere along the exhaust pipe or inserted in the exhaust pipe at the open end thereof.

The exhaust tube 4, the first catalyst device 5, the second catalyst device 6, and the muffler 7 are coupled via the flanges F, F that are fastened with bolts. The sensor units 11, 12, and 13 disposed between the constituent members of the exhaust path are each sandwiched by the flanges F, F. The flanges F, F are formed at either end of each constituent member of the exhaust path. The joint planes of the flanges are perpendicular to the center line of the exhaust path. Thus, the sensor units 11 to 13 are disposed in a manner that they intersect the exhaust path while they are sandwiched by the flanges F, F. The fourth sensor unit 14, which is used for analyzing the exhaust gas immediately before it is emitted to the atmosphere, may be disposed at an intermediate point of the exhaust pipe 8 protruding from the muffler 7, between the flanges F, F. The number of such sensor units is not particularly limited.

The individual sensor units 11 to 14 have identical configurations; therefore, one of them, the sensor unit 11, is described in the following with reference to FIG. 3. The sensor unit 11 includes a sensor main body 20 formed of a rectangular thin plate. The sensor main body has a through-hole 21 formed in the center thereof, the through-hole 21 having a diameter d which is the same as the internal diameter d of the circular cross section of the exhaust pipe, through which the exhaust gas passes. The plate-shaped sensor main body 20 has such a thickness as to allow for the fixed mounting of a laser light irradiation unit and a photoreceiving unit; the thickness, however, is desirably as small as possible. Preferably, the thickness of the sensor main body 20 is about 5 to 20 mm, for example. If the thickness exceeds 20 mm, disturbance tends to develop in the exhaust gas flow; if it is less than 5 mm, installation of the irradiation unit or the photoreceiving unit will be complicated. The sensor can be installed at any desired location on the exhaust path easily. The thickness of the sensor main body 20 may be set as desired.

Thus, the through-hole 21 is circularly shaped with the same diameter as the internal diameter of the exhaust pipe so as not to disturb the exhaust gas flow. As a result, the sensor units 11 to 14 disposed in the exhaust path do not disturb the exhaust gas flow, and pressure loss is minimized, thereby allowing for a smooth discharge of the gas. The sensor main body may be formed of a metal or ceramics plate; the material, however, is not particularly limited. The sensor main body 20 also has two sensor openings 22 and 23 formed in the center thickness-wise of the plate, penetrating the plate from its edge surface to the through-hole 21. The sensor openings 22 and 23 are opposite each other on a line passing through the center of the through-hole 21. The line connecting the sensor openings and the center line of the exhaust path are perpendicular to each other.

In the sensor unit 11, an optical fiber 25 (25A) is fixed in the sensor opening 22 as a laser light irradiation unit. As a photoreceiving unit for receiving the laser light that has passed through the exhaust gas present in the through-hole 21 after being emitted via the optical fiber 25, a detector 26 is fixed in the sensor opening 23. Thus, in the sensor main body 20, the optical fiber 25 on the irradiating end and the detector 26 as the photoreceiving unit are fixed opposite each other. The laser light emitted from the optical fiber 25 crosswise the exhaust path passes through the exhaust gas and is attenuated thereby, before it is received by the detector 26.

In other words, the laser light is emitted along a cross section perpendicular to the exhaust path, across which the light is received. In this way, the exhaust gas can be measured in one cross-section of the exhaust path in a spot-wise manner, so that it becomes possible to measure how the exhaust gas changes in a particular cross-section in the exhaust path instantaneously, thus enabling a real-time monitoring of the state of exhaust gas in a spot-wise manner. Because the analyzer enables the measurement of the concentration or temperature of the exhaust gas components immediately after discharge from the engine, or the concentration or temperature and the like of the exhaust gas components before and after the catalyzer disposed in the exhaust path, instantaneously in a spot-wise manner, extremely useful data can be acquired for the development of engines or exhaust gas purifiers, for example.

The sensor main body 20 is fixed between the flanges F, F, with gaskets 27, 27 disposed between each flange F and the sensor main body 20 and fixed with bolts and nuts, for example, which are not shown. The gaskets 27 are formed of asbestos, for example, and have a through-hole bored therein with the same diameter as the internal diameter of the exhaust tube. The structure prevents the leakage of exhaust gas when the sensor main body 20 is installed between the flanges F, F in the exhaust path, without much increase in the exhaust path length. FIG. 3 shows a configuration in which the sensor main body 20 is fixed between the flange F welded to the downstream end of the exhaust tube 4 and the flange F welded to the end of the exhaust pipe portion 5a upstream of the catalyst device 5, via gaskets 27,27.

The optical fiber 25 and the detector 26 are connected to a laser oscillation/photoreception controller 30. The laser oscillation/photoreception controller 30 emits infrared laser light that is delivered into the through-hole 21 of the sensor main body 20 via the optical fiber 25. The infrared laser light that has passed through the exhaust gas is received by the detector 26 on the receiving end and is then fed to the laser oscillation/photoreception controller 30 via signal line 28 (28A). The intensity of the light emitted by the optical fiber 25 and the intensity of the light received by the detector 26 via the exhaust gas, for example, are fed to the personal computer 45 as an analyzer. Thus, the exhaust gas analyzer 10 comprises a plurality of sensor units 11 to 14, the laser oscillation/photoreception controller 30, and the personal computer 45.

The laser oscillation/photoreception controller 30 is described with reference to FIG. 4. The laser oscillation/photoreception controller 30, as an irradiation device for emitting infrared laser light of a plurality of wavelengths, supplies signals with a plurality of frequencies from a signal generator, such as a function generator (not shown), for example, to a plurality of laser diodes LD1 to LD5. The laser diodes LD1 to LD5 then emit infrared laser light of a plurality of wavelengths corresponding to the different frequencies. The signal generator in the laser oscillation/photoreception controller 30 thus supplies signals of a plurality of frequencies to the laser diodes LD1 to LD5 which emit light. For example, LD1 emits infrared laser light of wavelength on the order of 1300 to 1330 nm, and LD2 emits infrared laser light of wavelength 1330 to 1360 nm, and so on, so that the wavelength bands in which the peak wavelengths of component gases to be detected exist are continuous.

The wavelength of the infrared laser light that is transmitted through exhaust gas is set in accordance with the exhaust gas component to be detected. When detecting carbon monoxide (CO), carbon dioxide ($CO_2$), ammonia ($NH_3$), methane ($CH_4$), and water ($H_2O$), infrared laser light of five wavelengths is used. For example, the wavelength suitable for the detection of ammonia is 1530 nm; the wavelength suitable for the detection of carbon monoxide is 1560 nm; and the wavelength suitable for the detection of carbon dioxide is 1570 nm. The wavelength suitable for the detection of methane is 1680 nm; the wavelength suitable for the detection of water is 1350 nm. When detecting the concentrations of other exhaust gas components, infrared laser light of different wavelengths in accordance with the exhaust gas components to be detected are used.

The infrared laser light emitted by each of the laser diodes LD1 to LD5 is guided by optical fibers 32 to demultiplexers 33, where the light is demultiplexed in accordance with the number of the sensor units. In the example of FIG. 4, the laser light emitted by each of the laser diodes LD1 to LD5 is demultiplexed into three components in view of the three sensor units 11 to 13. The laser light thus demultiplexed by the demultiplexers 33 is separated into signal light and measurement light by demultiplexers 34A, 34B, and 34C. The demultiplexers 34A are for the sensor unit 11; the demultiplexers 34B are for the sensor unit 12; and the demultiplexers 34C are for the sensor unit 13. The signal light separated by the five demultiplexers 34A for the sensor unit 11 is delivered by optical fibers and multiplexed by multiplexers 35A. The multiplexed signal light of a plurality of wavelength bands is then guided via an optical fiber 37A to a differential photodetector 40A, which will be described later. On the other hand, the measurement light separated by the five demultiplexers 34A is passed through optical fibers and multiplexed in a multiplexer 36A, and the multiplexed light is then guided to the irradiation unit of the sensor unit 11 via an optical fiber 25A.

The infrared laser light separated by the demultiplexers 33 is separated into signal lights and measurement light by five demultiplexers 34B for the sensor unit 12. The signal light is multiplexed by a multiplexer 35B into signal light of a plurality of wavelength bands, and the multiplexed light is then guided via an optical fiber 37B to a differential photodetector 40B. The measurement light separated by the five demultiplexers 34B is multiplexed in the multiplexer 36B, and the multiplexed light is guided via an optical fiber 25B to the irradiation unit of the sensor unit 12. The infrared laser light separated by the demultiplexers 33 is also separated into signal light and measurement light by five demultiplexers 34C for the sensor unit 13. The signal light is multiplexed by a multiplexer 35C into signal light of a plurality of wavelength bands, and the multiplexed light is guided by an optical fiber 37C to a differential photodetector 40C. The measurement light separated by the five demultiplexers 34C is multiplexed by a multiplexer 36C, and the multiplexed light is guided by an optical fiber 25C to the irradiation unit for the sensor unit 13.

FIG. 4 shows three sensor units 11 to 13. When additional sensor units 14 are to be installed, the infrared laser light is demultiplexed by the demultiplexers 33 into additional laser light components. The thus demultiplexed laser light components are divided into measurement light and signal light by additional demultiplexers 34. The signal laser light is multiplexed by additional multiplexers 35 and then guided to a differential photodetector, while the measurement laser light is guided to the additional sensor units 14.

The detectors 26A, 26B, and 26C on the receiving end connected to the photoreceiving units of the sensor units 11 to 13 are connected via signal lines 28A, 28B, and 28C to the differential photodetectors 40A, 40B, and 40C of the laser oscillation/photoreception controller 30. The signal light is guided via the optical fibers 37A, 37B, and 37C to the differential photodetectors 40A, 40B, and 40C. In the differential photodetectors, the difference between the transmitted laser light attenuated by transmission through the exhaust gas and the signal laser light that has not passed through the exhaust gas is obtained. The signal laser light is fed to a photodiode, for example, whose output is amplified by a preamplifier (not shown) and the amplified signal is fed via an A/D converter to the personal computer 45, i.e., the signal analyzer. In the personal computer 45, the concentration of an exhaust gas component and the temperature of the exhaust gas, for example, are calculated from the input signal, so as to analyze the exhaust gas.

In accordance with the exhaust gas analyzer 10 of the present invention, infrared laser light, for example, is passed through exhaust gas, and the concentration of an exhaust gas component is calculated on the basis of the intensity of the incident light and the intensity of the transmitted light that has passed through the exhaust gas, so as to analyze the exhaust gas. Concentration C of an exhaust gas component is calculated from the following equation (1):

$$C = -\ln(I/I_0)/kL \qquad (1)$$

where I is the transmitted light intensity, $I_0$ is the incident light intensity, k is absorptance, and L is the transmission distance. Thus, concentration C of an exhaust gas component is calculated on the basis of the ratio of transmitted light intensity (I) to incident (signal) light intensity ($I_0$); namely, the signal intensity ratio ($I/I_0$). The transmitted light intensity $I_0$ is outputted via the detectors 26A, 26B, and 26C; the incident light intensity $I_0$ is outputted via the optical fibers 37A, 37B, and 37C, by photoelectric converters, such as photodiodes in the differential photodetectors 40, for example. In the present embodiment, the incident light intensity $I_0$ is the intensity of the signal light that is not passed through the exhaust gas.

The operation of the exhaust gas analyzer 10 that is configured as described above is described in the following. When measuring the concentration of an exhaust gas component, the signal generator in the laser oscillation/photoreception controller 30 is activated to supply signals to the individual laser diodes LD1 to LD5 so as to cause them to emit infrared laser light of predetermined wavelengths. The infrared laser light emitted by each of the laser diodes LD1 to LD5 is delivered via the optical fibers 32 to the demultiplexers 33, where the light is demultiplexed in accordance with the number of the sensor units.

The demultiplexed infrared laser light is demultiplexed by the demultiplexers 34A, 34B, and 34C into measurement light and signal light. With reference to a single sensor unit 11, the signal light demultiplexed by the five demultiplexers 34A is multiplexed by the multiplexer 35A into signal laser light, which is guided to the differential photodetector 40A. The measurement light demultiplexed by the five demultiplexers 34A is multiplexed by the multiplexer 36A into measurement laser light, which is guided via the optical fiber 25A to the irradiation unit of the sensor unit 11. The same applies to the other sensor units 12 and 13; namely, after demultiplexing in the demultiplexers 33, the laser light is demultiplexed by the demultiplexers 34B and 34C into signal light and measurement light. After multiplexing by the multiplexers 35B and 35C, the signal light is guided to the differential photodetectors 40B and 40C while the measurement light is guided to the sensor units 12 and 13.

The infrared laser light R emitted by the optical fibers 25A, 25B, and 25C in the sensor units 11 to 13 for measurement is shone into the through-hole 21 where the exhaust gas passes. The infrared laser light R travels across the through-hole 21 in the exhaust path, and is then transmitted through the exhaust gas while being attenuated thereby. The transmitted, attenuated light is then received by the detectors 26A, 26B, and 26C, or the photoreceiving units. Thus, the infrared laser light R for measurement is received after traveling across the through-hole 21, which is part of the exhaust path, in a plane perpendicular to the exhaust path. As a result, the concentration or temperature of an exhaust gas component in a perpendicular cross section can be measured in a spot-wise manner. In other words, instead of measuring the concentration or temperature of an exhaust gas component within a certain length range along the exhaust path, the invention makes it possible to measure the concentration or temperature of an exhaust gas component with respect to a predetermined single plane intersecting the exhaust path, thereby allowing a spot-wise measurement.

Because the plane in which the laser light is transmitted through exhaust gas is perpendicular to the direction of flow of exhaust gas, the exhaust gas emitted by the engine can be measured in a time-series manner. As a result, it becomes possible to evaluate the performance of the engine exhaust system as well as that of the engine itself highly accurately.

The measurement infrared laser light R that has passed through the exhaust gas, been attenuated thereby, and reached the photoreceiving units are converted into electric signals by the detectors 26A, 26B, and 26C. The electric signals are then supplied via the signal lines 28A, 28B, and 28C to the differential photodetectors 40A, 40B, and 40C. On the other hand, the signal laser light is guided to the differential photodetectors 40A, 40B, and 40C, by which the difference between the transmitted light and the signal light is obtained for each of a plurality of wavelength components, so as to detect the peak wavelength of a particular gas component in the transmitted light. In this way, the outputs of the differential photodetectors are fed to the signal analyzer, or the personal computer 45. In the personal computer 45, based on the peak wavelength of each of the plurality of frequency bands that have been received, the concentration and temperature, for example, of the exhaust gas component are measured and analyzed.

Figure 5:
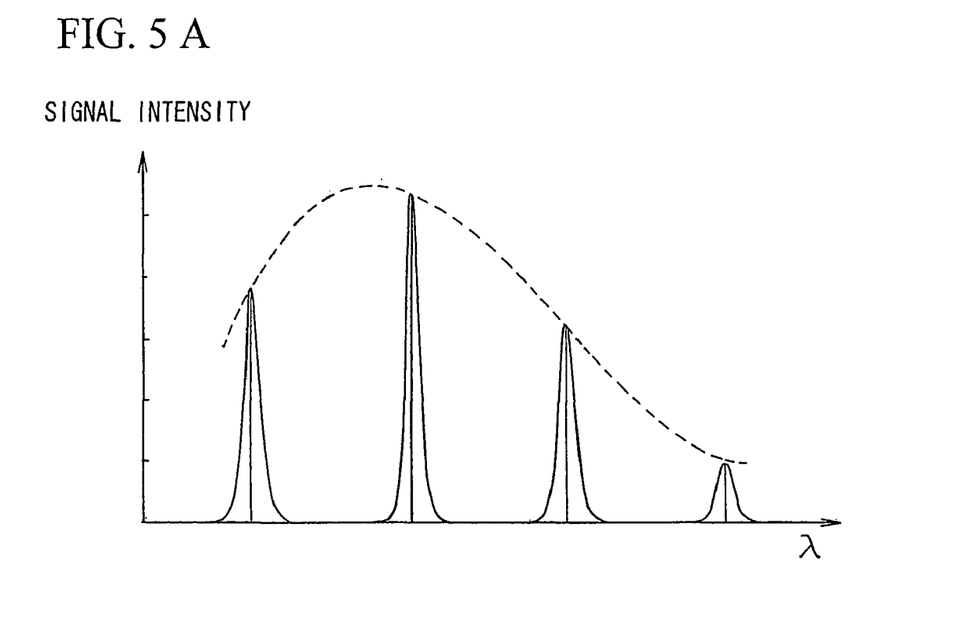
FIG. 5 shows the influence of pressure in absorption spectrum.

Gases have their own unique absorption wavelength bands, where a number of absorption lines are present, as shown in FIG. 5, for example. FIG. 5a shows the signal intensity (=the proportion of the number of molecules) at low temperature; FIG. 5b shows the signal intensity at high temperature. As shown, the signal intensity varies depending on temperature, so that by measuring the signal intensity ratio, the temperature of the exhaust gas at the time of measurement can be calculated.

Figure 6A:
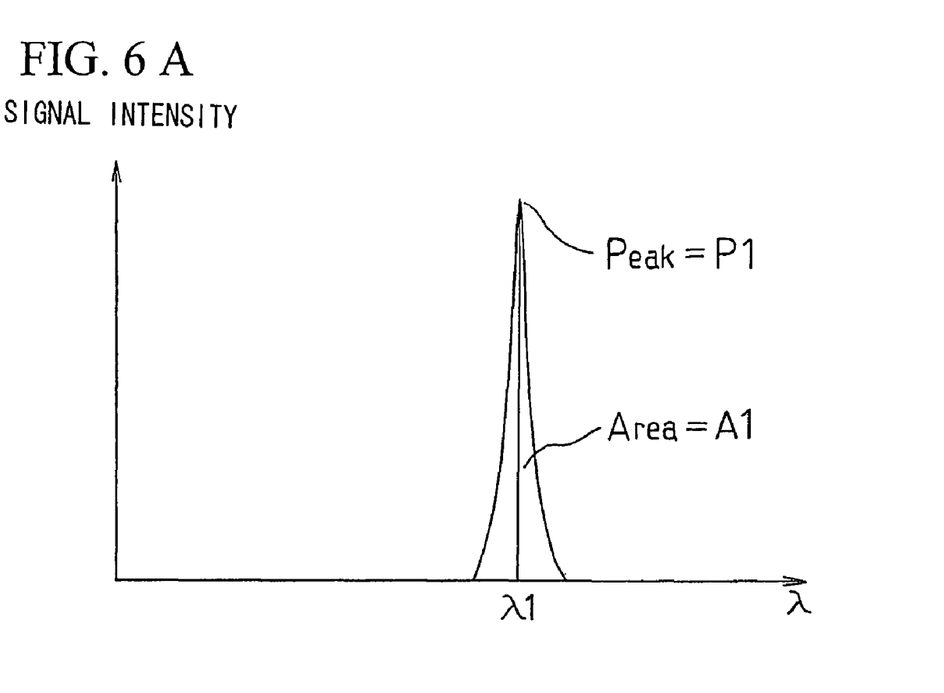
FIG. 6a is a chart for the description of how the concentration of a gas component is calculated from an absorption spectrum according to prior art.
Figure 6B:
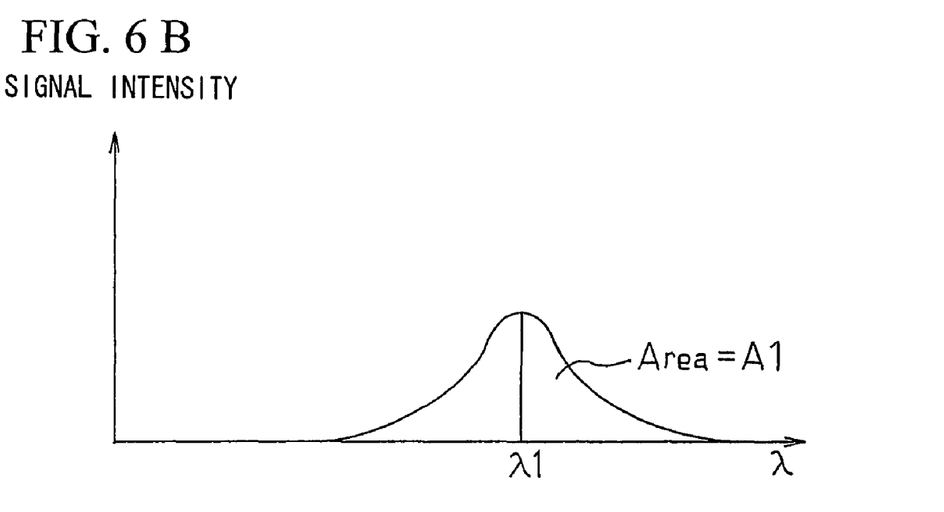
FIG. 6b is a chart for the description of how the gas concentration is calculated from an absorption spectrum according to the present invention.

Then, as shown in FIG. 6, by sweeping the oscillation wavelength of the laser light with respect to one of the absorption lines, such as the wavelength $\lambda 1$, absorption is measured. By obtaining the ratio of this waveform to the waveform of the signal laser light, a spectral profile is measured. For temperature measurement, such spectral profile can be measured with respect to two different absorption lines $\lambda 1$ and $\lambda 2$, and then their areal ratio A1/A2 (or the ratio of height of one peak to the other, P1/P2). In the conventional wavelength modulation method, as shown in FIG. 6a, the concentration of a component has been calculated from the radius of curvature at the tip of an absorption spectral peak. In accordance with the invention, as shown in FIG. 6b, the concentration of a component is calculated from the area of the absorption spectrum, which makes it possible to calculate the concentration of an exhaust gas component without much influence of pressure.

In the exhaust gas analyzer 10 of the present embodiment, it is possible to measure the concentration or temperature of an exhaust gas component at a plurality of locations along the exhaust path of the engine 2 in a spot-wise manner, in one cross-section of the exhaust path and in real-time. Thus, the exhaust gas analyzer 10 enables the instantaneous measurement of: the temperature of the exhaust gas immediately after being emitted from the engine, or the concentration of an exhaust gas component therein; the temperature of the exhaust gas, or the concentration of an exhaust gas component therein, that has passed through the first catalyst device 5, second catalyst device 6, and the muffler 7; or the condition of the exhaust gas immediately before being emitted via the exhaust pipe 8 into the atmosphere. Because the exhaust gas analyzer 10 of the present embodiment enables the measurement of the concentration of an exhaust gas component along the exhaust path in any desired cross section thereof, measurements can be taken in a timely fashion, thereby significantly reducing the period required for the development of engines or purifying devices accompanying them.

The exhaust gas analyzer 10 of the present embodiment is configured such that no reference gas or the like is required, and the sensor unit for the analysis of exhaust gas is made compact in size. Thus, the exhaust gas analyzer 10 can be easily installed on an automobile, for example, for the analysis of exhaust gas emitted by the automobile. Thus, the exhaust gas can be analyzed in real-time as it is emitted by the automobile. Furthermore, a long transmission distance of the laser light in the exhaust gas can be obtained, so that high measurement accuracy can be achieved and the need for reference gas or the like during measurement can be eliminated, thereby reducing the cost for exhaust gas analysis.

Specifically, because the sensor units 11 to 14 fixed in the exhaust path each comprise a thin, plate-shaped sensor main body 20, the sensor units can be installed with little change caused in fluid resistance, for example, in the exhaust path. The exhaust gas analyzer 10 is capable of measuring in a high temperature condition, so that the temperature of the exhaust gas or the concentration of an exhaust gas component therein immediately after being emitted by the engine 2 can be measured for analysis. By increasing the number of wavelengths in laser light, more components contained in the exhaust gas can be analyzed easily.

Figure 7:
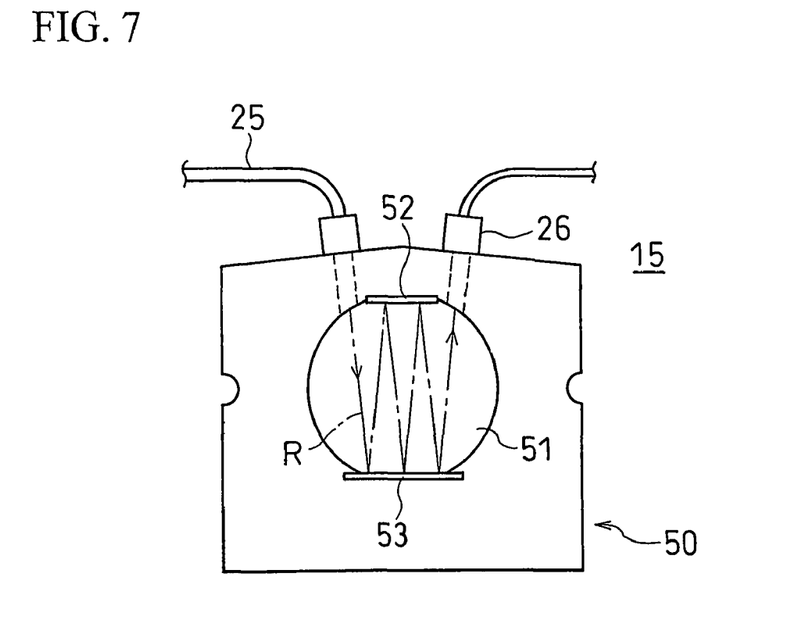
FIG. 7 shows a front view of the sensor unit of the exhaust gas analyzer according to another embodiment of the invention.

With reference to FIG. 7, another embodiment of the invention is described. FIG. 7 shows a cross section of the main portion of the sensor unit used in the exhaust gas analyzer according to the embodiment. This embodiment is characterized in that, as compared with the foregoing embodiment, a plurality of sensor units 15 are configured such that a detector 26 does not directly receive the infrared laser light R that has passed through exhaust gas after being emitted by the optical fiber 25, but rather the detector 26 receives the infrared laser light R that has been reflected a plurality of times within the through-hole. The reflecting surfaces that reflect the infrared laser light comprise two reflecting plates disposed opposite each other in the through-hole. The infrared laser light is received after being repeatedly reflected between the two reflecting plates. The other portions of the sensor unit substantially equivalent to the corresponding portions of the foregoing embodiment are designated by similar numerals; their detailed descriptions are omitted.

In the present embodiment shown in FIG. 7, a through-hole 51 is formed in the sensor main body 50 of the sensor unit 15 at the center thereof, for the passage of exhaust gas. Within the through-hole 51, upper and lower reflecting plates 52 and 53 are disposed opposite each other and in parallel, each facing the through-hole 51. The two reflecting plates are fixed in parallel such that the laser light can travel perpendicular to the exhaust path within the through-hole 51. Specifically, the infrared laser light R emitted by the optical fiber 25 on the emitting end is initially reflected by the lower reflecting plate 53 upward; it is then reflected by the upper reflecting plate 52 downward. The infrared laser light R is thus alternately reflected by the two reflecting plates 52 and 53 before it reaches the detector 26 on the receiving end. Thus, the laser light is reflected a plurality of times in a cross-section perpendicular to the exhaust path before it is received by the detector 26.

Preferably, the thickness of the sensor main body 50, which is made of a thin plate, is 5 to 20 mm as in the foregoing embodiment; the material of the thin plate is preferably metal or ceramics. The sensor main body 50 is fixedly sandwiched between flanges F, F, not shown, when it is installed in the exhaust path. It has semicircular notches formed in two of its sides, one on the left and the other on the right, at positions corresponding to the bolts connecting the flanges. The through-hole 51 in the sensor main body 50 is basically formed in the same shape as the cross-sectional shape of the exhaust path and with the same diameter; additionally, flat mounting portions are formed at the top and bottom of the opening for fixing the reflecting plates 52 and 53. Such circular shape with partial flat portions is substantially included in the "shape conforming to the cross-sectional shape of the exhaust path."

The optical fiber 25 on the emitting end is fixed with an outward inclination of about 6° with respect to a line perpendicular to the reflecting plates; the detector 26 on the receiving end is also fixed with an outward inclination of about 6°. Because the optical fiber 25 and the detector 26 are disposed at an angle with respect to the two reflecting plates 52 and 53, the infrared laser light R emitted by the optical fiber 25 on the emitting end is repeatedly reflected by the upper and lower reflecting plates, before it is eventually received by the detector 26 on the receiving end after traveling the long optical path through the exhaust gas. Thus, the infrared laser light, as it is repeatedly reflected by the reflecting plates 52 and 53, can travel a longer optical path than the diameter of the through-hole 51 at the center. As a result, the amount of attenuation in the infrared laser light caused during its transmission through the exhaust gas increases, whereby the accuracy of measurement of the concentration or the like of a component contained in the exhaust gas can be improved. The number of reflections of the infrared laser light between the reflecting plates can be changed as needed depending on the concentration of a component contained in the exhaust gas or the required measurement accuracy, for example.

The reflecting plates 52 and 53 are each rectangularly formed, with the substrate as a base being made of material having small thermal expansion, such as SiC, $SiO_2$, or sapphire. On this substrate, a thin film of gold or platinum is formed as a reflecting surface, on top of which a thin film of $MgF_2$ or $SiO_2$ is formed as a protection layer. In the present embodiment, the reflecting plates 52 and 53 are fixed on the sensor main body 50 with cement or the like; it is preferable, however, to detachably mount the reflecting plates with screws, springs, or the like, so as to allow them to be removed for cleaning after exposure to exhaust gas during, the operation of the engine.

In the sensor unit 15 of the present embodiment, the infrared laser light emitted by the irradiation unit, i.e., the optical fiber 25 is repeatedly and alternately reflected by the opposed reflecting plates 52 and 53, so that the optical path, namely, the transmission distance of the laser light in the exhaust gas, can be increased. Such extension in the distance traveled by the infrared laser light as it is transmitted through exhaust gas causes an increase in attenuation, thereby allowing an instantaneous measurement of the concentration of an exhaust gas component with high accuracy. The through-hole 51 formed in the sensor main body 50 is basically circular with the same diameter as that of the circular cross-section of the exhaust path. This allows the exhaust gas to flow without disturbance, and also makes it possible to disregard any change in exhaust resistance when the sensor unit 15 is fixed in the existing exhaust path. Furthermore, because the reflecting plates 52 and 53 comprise flat plates, they can be easily manufactured, readily removed from the sensor main body 50, and replaced.

In the sensor unit 15 of the present embodiment, the ratio of the optical intensity $I_0$ of the signal laser light to the transmitted light intensity I of the measurement infrared laser light R ($I/I_0$), is calculated, and, based on the signal intensity ratio, the concentration of an exhaust gas component is calculated. Because the transmitted light intensity is greatly attenuated by the increase in the transmission distance due to the multiple reflections, the concentration or temperature of an exhaust gas component can be measured with high accuracy. While the infrared laser light R is attenuated by the repeated reflections by the reflecting surfaces 52 and 53, preferably the ratio of the intensity of light received by the detector 26 to the intensity of the light emitted by the optical fiber 25 in the absence of exhaust gas is 30% or more. This is because if the ratio drops below 30%, it becomes difficult to distinguish useful signal from noise.

Figure 8:
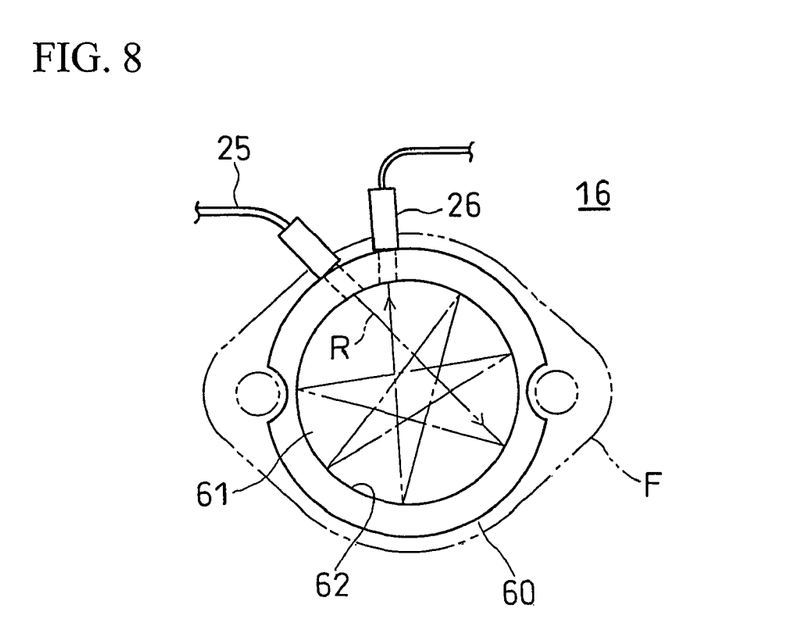
FIG. 8 shows a front view of the sensor unit of the exhaust gas analyzer according to still another embodiment of the invention.

The sensor unit of the exhaust gas analyzer according to still another embodiment of the invention is described with reference to FIG. 8. The sensor unit 16 according to this embodiment has a reflecting surface 62 formed on the inside of a through-hole 61 formed in a sensor main body 60. The reflecting surface 62 is formed as a reflector of the infrared laser light R that is passed through exhaust gas. Specifically, the optical fiber 25 on the emitting end and the detector 26 on the receiving end are mounted on the sensor main body 60. The infrared laser light R emitted by the optical fiber 25 on the emitting end is reflected by the reflecting surface 62 formed on the inside of the through-hole 61 a plurality of times, and is then received by the detector 26 on the receiving end.

The through-hole 61 is circularly formed with the same diameter as that of the circular cross-section of the exhaust path. The sensor main body 60 is fixed between the flanges F, F via which the exhaust path components are connected. The formation of the reflecting surface 62 on the inside of the through-hole 61 eliminates the need for mirrors or the like as a reflecting member separate from the sensor main body 60, thereby contributing to the simplification of structure. At the same time, because the shape of the through-hole 61 can be made identical to the cross-sectional shape of the exhaust pipe, no disturbance is caused in the flow of exhaust gas when the sensor is installed in the existing exhaust path, and no drop in exhaust efficiency is caused.

The reflecting surface 62 formed on the inside of the through-hole 61 comprises a mirror-finished circumferential surface, on which a thin film of gold or platinum is formed. A protection layer is further formed on top, consisting of a thin film of $MgF_2$ or $SiO_2$. Preferably, the reflecting surface 62 has high reflectance so as to reflect the infrared laser light efficiently. Also preferably, the reflecting surface is cleaned as needed by removing the sensor main body 60 from the flanges F, F, as the reflecting surface is exposed to exhaust gas during the operation of the engine and dirt becomes attached thereto. By wiping the protection layer by which the reflecting surface 62 is covered, the dirt that has attached can be easily removed to improve reflectance.

In this configuration, the infrared laser light R emitted by the optical fiber 25 on the emitting end is reflected by the reflecting surface 62 a plurality of times within the through-hole 61, before it is received by the detector 26 on the receiving end via a long optical path. Thus, the laser light travels the long transmission distance through the exhaust gas in the through-hole 61. As a result, the laser light can be effectively utilized as in the foregoing embodiment, and so an enhanced measurement accuracy can be obtained. Furthermore, because the cross-sectional shape of the exhaust path is identical to the cross-sectional shape of the through-hole in the sensor unit, no disturbance is caused in exhaust gas flow, and the exhaust loss due to the installment of the sensor unit in the exhaust path can be eliminated.

The cross-sectional shape of the exhaust path, which has been described to be circular, may not be circular in a perfect sense but may be elliptical, for example; it does not even have to be circular but may be rectangular or polygonal. In such cases, a rectangular or polygonal through-hole is formed in the sensor main body of the sensor unit, and the infrared laser light is reflected by one reflecting surface after another formed on each of the planes of which the polygon is formed. As a result, the transmission distance of the laser light that is transmitted through the exhaust gas can be extended. When the individual surfaces of such through-hole are to be used as reflecting surfaces, the through-hole preferably consists of a polygon having an odd number of sides, such as a pentagon, for example. The number of such surfaces may be further increased so as to increase the transmission distance through the exhaust gas. The outer shape of the sensor main body is not limited to circular but may be rectangular, or any other suitable shape.

While the invention has been described above by way of embodiments, the invention is not limited to such embodiments. Various changes or modifications may be made to the invention without departing from the spirit and scope of the invention as set forth in the appended claims. For example, the exhaust gas component to be measured may be nitride oxides (NOx); in this case it goes without saying that the infrared laser light that is passed through the exhaust gas should have a wavelength adapted to NOx. The laser light emitted by the irradiation unit is not limited to infrared laser light but may be visible laser light or ultraviolet laser light.

While in the foregoing embodiments an optical fiber was mounted on the sensor main body of the sensor unit as the irradiation unit, and a detector was installed as the photoreceiving unit, the sensor main body may be directly equipped with an irradiation unit such as a laser diode, and, instead of the detector such as the photodiode, an optical fiber may be installed for photoreceiving purposes. Alternatively, the irradiation unit consisting of an optical fiber may be equipped with a collimator lens, so that the laser light is emitted into the through-hole via the collimator lens. Further alternatively, the sensor unit may be disposed between the cylinder block of an internal combustion engine and the exhaust manifold.

INDUSTRIAL APPLICABILITY

The exhaust gas analyzer of the invention can be used for measuring the concentration or temperature of an exhaust gas component in a cross-sectional area perpendicular to the exhaust path. It can be used for measuring the concentration, for example, of an exhaust gas component in the exhaust path in a predetermined cross-section in a spot-wise manner, thus enabling the real-time measurement of the condition of the exhaust gas in the exhaust path with high accuracy. Thus, the invention enables a real-time exhaust gas analysis, which is extremely useful for the development of internal combustion engines or exhaust gas purifying devices.

For example, the exhaust gas analyzer of the invention can be used for the exhaust gas analysis for combustion equipment, such as boilers. In addition to the exhaust gas analysis for automobiles, the invention can also be used for the exhaust gas analysis for internal combustion engines in ships or electric power generators. Furthermore, apart from the exhaust gas analysis for gasoline engines, the invention can be used for the exhaust gas analysis for diesel engines or other types of internal combustion engines.

The invention claimed is:

1. An exhaust gas analyzer comprising a plurality of sensor units disposed at a plurality of locations along an exhaust path via which exhaust gas is discharged from an internal combustion engine,
   each one of the plurality of sensor units comprising:
      an irradiation unit that applies a laser light in a direction perpendicular to a direction of extension of the exhaust path at a position of the exhaust path where the irradiation unit is disposed, a photoreceiving unit for receiving the laser light emitted by the irradiation unit that has been transmitted through the exhaust gas, a plate-shaped main body, and a through-hole formed in the main body allowing passage of the exhaust gas, wherein the through-hole is formed in a shape matched with a cross-sectional shape of the exhaust path,
   wherein for each one of the plurality of sensor units, the concentration or temperature of an exhaust gas component is measured on the basis of the laser light received by the photoreceiving unit for analyzing the exhaust gas,
   wherein for each one of the plurality of sensor units, the laser light is shone by the irradiation unit into the through-hole and is received by the photoreceiving unit across the exhaust path, and
   wherein for each one of the plurality of sensor units, the plate-shaped main body is sandwiched in-between a pair of flanges extending from components along the exhaust path,
   wherein the exhaust gas analyzer further comprises a controller configured to emit, for each one of the plurality of sensor units, the laser light into the through hole via the irradiation unit, the controller comprising a plurality of laser diodes, each laser diode being connected to one of a plurality of first demultiplexers, each one of the plurality of first demultiplexers being connected to a plurality of second demultiplexers, the plurality of second demultiplexers being configured to separate the laser light for each one of the plurality of sensor units into signal light and measurement light, and the controller further comprising a plurality of multiplexers, each one of the plurality of multiplexers being configured to receive and multiplex either the signal light or the measurement light.

2. The exhaust gas analyzer according to claim 1, wherein for each one of the plurality of sensor units, the laser light comprises a multiplexing of laser light having absorption wavelengths matched with a plurality of components of the exhaust gas.

3. The exhaust gas analyzer according to claim 1, wherein for each one of the plurality of sensor units, the plate-shaped main body has a substantially rectangular shape.

4. The exhaust gas analyzer according to claim 1, wherein for each one of the plurality of sensor units, the plate-shaped main body has a thickness in a range of about 5 mm to 20 mm.

5. The exhaust gas analyzer according to claim 1, wherein for each one of the plurality of sensor units, a respective gasket is disposed in-between each of the flanges and the plate-shaped main body.

6. The exhaust gas analyzer according to claim 1, wherein for each one of the plurality of sensor units, the plate-shaped main body has notches disposed along sides of the plate-shaped main body at positions corresponding to locations of bolts connecting the flanges.

7. The exhaust gas analyzer according to claim 1, wherein one of the plurality of first demultiplexers of the controller is configured to demultiplex the laser light for each one of the plurality of sensors into a number of components equal to the number of sensor units.

8. The exhaust gas analyzer according to claim 1, wherein the exhaust path has a circular cross-sectional shape, and wherein the through-hole formed in the main body of each of the plurality of sensor units has a substantially circular shape with a diameter which is the same as a diameter of the circular cross-sectional shape of the exhaust path.

9. The exhaust gas analyzer according to claim 1, further comprising a plurality of differential photodetectors, each one of the plurality of differential photodetectors being connected to each one of the plurality of sensor units, wherein each one of the plurality of differential photodetectors is configured to obtain a difference in wavelength between the measurement light and the signal light for each one of the plurality of sensor units, and to output the difference to a signal analyzer.

10. The exhaust gas analyzer according to claim 1 or 8, wherein for each one of the plurality of sensor units, the through-hole has a reflecting portion formed on an internal circumferential surface thereof, wherein the laser light emitted by the irradiation unit is reflected by the reflecting portion and then received by the photoreceiving unit.

11. The exhaust gas analyzer according to claim 10, wherein for each one of the plurality of sensor units, the reflecting portion comprises two reflecting plates disposed in parallel and opposite each other such that the two reflective plates face an inside of the through-hole, wherein for each one of the plurality of sensor units, the laser light is reflected in a direction perpendicular to the exhaust path.

12. The exhaust gas analyzer according to claim 9, wherein the plurality of differential photodetectors are further configured to detect a peak wavelength of a particular gas component in the measurement light.

13. The exhaust gas analyzer according to claim 9, wherein two of the plurality of multiplexers are provided for each one of the plurality of sensor units, wherein a first of the two multiplexers multiplexes the signal light to one of the plurality of differential photodetectors, and wherein a second of the two multiplexers multiplexes the measurement light to one of the plurality of sensor units connected to the one of the plurality of differential photodetectors.

* * * * *